United States Patent [19]

Kyburz et al.

[11] 4,369,139

[45] Jan. 18, 1983

[54] 1-(p-METHOXY p-HYDROXY, AND p-BENZYLOXY BENZOYL)-2-PYRROLIDINONES

[75] Inventors: Emilio Kyburz, Reinach; Werner Aschwanden, Ettingen, both of Switzerland

[73] Assignee: Hoffmann-La Roche Inc., Nutley, N.J.

[21] Appl. No.: 168,906

[22] Filed: Jul. 14, 1980

Related U.S. Application Data

[63] Continuation of Ser. No. 8,673, Feb. 2, 1979, abandoned.

[30] Foreign Application Priority Data

Feb. 10, 1978 [CH] Switzerland .......................... 1403/78
Nov. 22, 1978 [CH] Switzerland ........................ 11981/78

[51] Int. Cl.$^3$ .................... C07D 207/27; A61D 31/40
[52] U.S. Cl. ..................................... 548/539; 424/274
[58] Field of Search ............................... 260/326.5 FL

[56] References Cited

FOREIGN PATENT DOCUMENTS 2413935 10/1975 Fed. Rep. of Germany .

OTHER PUBLICATIONS

Jones et al, "Chem. of Pyrroles", pp. 379, 380, 398 and 399, Academic Press, (1977), N.Y.
Merck Index, 9th Ed., p. 975, Item 7282 (1976) Merck & Co.
Shklob et al, Zh. Obshch. Khim 35, pp. 1389–1398 (1965) CA 63 (1965) 16256c.

*Primary Examiner*—Donald G. Daus
*Assistant Examiner*—D. B. Springer
*Attorney, Agent, or Firm*—Jon S. Saxe; George M. Gould; Peter R. Shearer

[57] ABSTRACT 1-(p-methoxybenzoyl)-2-pyrrolidinone and intermediates useful in its preparation are described. The 1-(p-methoxybenzoyl)-2-pyrrolidinone is useful in the prevention of cerebral insufficiency.

3 Claims, No Drawings

1-(p-METHOXY p-HYDROXY, AND p-BENZYLOXY BENZOYL)-2-PYRROLIDINONES

This is a continuation, of application Ser. No. 8,673 filed Feb. 2, 1979, abandoned.

BRIEF SUMMARY OF THE INVENTION

The invention relates to the compound 1-(p-methoxybenzoyl)-2-pyrrolidinone which has the formula

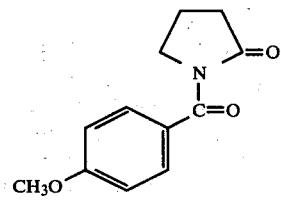

In another aspect, the invention relates to processes of preparing 1-(p-methoxybenzoyl)-2-pyrrolidinone and to intermediates useful therein.

In yet another aspect, the invention relates to the use of 1-(p-methoxybenzoyl)-2-pyrrolidinone as an agent for the control or prevention of cerebral insufficiency.

DETAILED DESCRIPTION OF THE INVENTION

This invention relates to the compound 1-(p-methoxybenzoyl)-2-pyrrolidinone, which has the formula

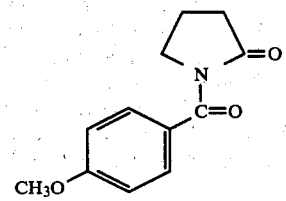

The 1-(p-methoxybenzoyl)-2-pyrrolidinone can be prepared by processes which comprise the following:

(a) acylating 2-pyrrolidinone in the 1-position;

(b) methylating 1-(p-hydroxybenzoyl)-2-pyrrolidinone;

(c) reducing a 2-pyrrolinone derivative of the formula

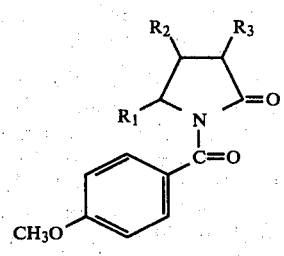

wherein one of $R_1$ and $R_3$ is hydrogen and the other, together with $R_2$ is a second carbon-carbon bond, or a mixture of the two derivatives defined by formula II;

(d) cyclizing 4-(p-methoxybenzoylamino)butyric acid; or (e) hydrolyzing a compound of the formula

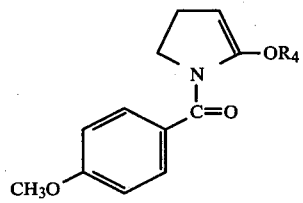

wherein $R_4$ is lower alkyl.

According to process embodiment (a) above, the compound of formula I can be prepared by acylating 2-pyrrolidinone in the 1-position, that is, the hydrogen atom in the 1-position of 2-pyrrolidinone is replaced by a p-methoxybenzoyl group. The acylation is carried out using known methods. The acylating agent used is a reactive derivative of p-methoxybenzoic acid. Suitable acylating agents include, for example, reactive halides of p-methoxybenzoic acid, preferably p-methoxybenzoyl chloride, and reactive esters of p-methoxybenzoic acid, for example, polyhalophenyl esters, such as p-methoxybenzoic acid pentachlorophenyl ester.

The acylation of 2-pyrrolidinone with p-methoxybenzoyl chloride is conveniently carried out in the presence of an inert organic solvent and a base. Suitable solvents include ethers such as diethyl ether, tetrahydrofuran, dioxane, etc, and aromatic hydrocarbons, such as toluene or the like. Suitable bases include tertiary amines, such as triethylamine and the like. The acylation can also be carried out in pyridine which functions as both the solvent and the base. Neither the presence of a solvent nor the presence of a base is, however, required. The starting materials can be heated together at about 80°–90° C. for about one hour or they can be heated at reflux for several hours in a suitable solvent, for example, an ether, an aromatic hydrocarbon, or the like.

Alternatively, the 2-pyrrolidinone can first be treated with a base capable of removing the hydrogen atom from the nitrogen atom in the 1-position and then be reacted with p-methoxybenzoyl chloride. In this process, the base which is used can be, for example, an alkali metal hydride such as sodium hydride or the like, and the solvent can be dimethylformamide, an aromatic hydrocarbon such as benzene, or the like.

The 1-(p-methoxybenzoyl)-2-pyrrolidinone can also be prepared by acylating a reactive 2-pyrrolidinone derivative having a readily cleavable group, for example, a readily cleavable metal-organic group, such as a trialkylsilyl group, bonded to the nitrogen atom. A preferred reactive derivative of this type is 1-trimethylsilyl-2-pyrrolidinone.

According to process embodiment (b) above, 1-(p-methoxybenzoyl)-2-pyrrolidinone can be prepared by methylating 1-(p-hydroxybenzoyl)-2-pyrrolidinone. The methylation is carried out using known methods. Suitable methylating agents are, for example, dimethylsulfate, methyl iodide and the like. When such methylating agents are used, the methylation is conveniently carried out in the presence of a base, for example, sodium methylate, sodium hydride or the like, and an organic solvent which is inert under the methylation conditions, for example, dimethylformamide, or an aromatic hydrocarbon such as benzene, toluene or the like. Diazomethane is also a suitable methylating agent. When diazomethane is used, the methylation is conveniently carried out in an etheric solution, for example, in tetrahydrofuran, diethyl ether or the like or mixtures of such ethers. The 1-(p-hydroxybenzoyl)-2-pyrrolidinone used as the starting material can be prepared, for example, by replacing the hydrogen atom bonded to the nitrogen atom of the 2-pyrrolidinone with a p-benzyloxybenzoyl group. This can be accomplished by using p-benzyloxybenzoyl chloride in an analogous manner to that described previously in connection with process embodiment (a) above. The resultant 1-(p-benzyloxybenzoyl)-2-pyrrolidinone is debenzylated according to known methods, for example, by hydrogenation in the presence of a suitable catalyst such as palladium. The 1-(p-hydroxybenzoyl)-2-pyrrolidinone and 1-(p-benzyloxybenzoyl)-2-pyrrolidinone are novel compounds within the scope of the invention.

According to process embodiment (c) above, the 1-(p-methoxybenzoyl)-2-pyrrolidinone can be prepared by reducing a 2-pyrrolinone derivative of formula II or a mixture of the two derivatives defined by formula II. The reduction is preferably carried out using catalytically activated hydrogen in an organic solvent which is inert under the reduction conditions. Suitable reduction catalysts include, for example, palladium, platinum and the like. Suitable reaction solvents include, for example, ethyl acetate, alcohols such as methanol, ethanol or the like, and ethers such as tetrahydrofuran.

The compounds of formula II are novel compounds within the scope of the invention which can be conveniently prepared by reacting 5-oxo-3-pyrrolidinyl acetate, or another suitable ester of 5-oxo-3-pyrrolidinol, with trimethylchlorosilane or the like, reacting the resultant compound, for example, 5-oxo-1-trimethylsilyl-3-pyrrolidinyl acetate, with a suitable p-methoxybenzoylating agent such as p-methoxybenzoyl chloride and treating the resultant product under mildly basic conditions with, for example, sodium bicarbonate. Alternatively, the compounds of formula II can be prepared by acylating, at the 1-position, a compound of the formula

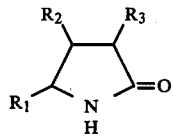

IV wherein $R_1$, $R_2$ and $R_3$ are as previously described, or a mixture of the two compounds defined by formula IV.

According to process embodiment (d) above, 1-(p-methoxybenzoyl)-2-pyrrolidinone can be prepared by cyclizing 4-(p-methoxybenzoylamino)butyric acid. In this cyclization, one mole of water is cleaved off. The cyclization is carried out by heating and/or treatment with a water-cleaving agent such as polyphosphoric acid, phosphorus pentachloride, thionyl chloride or the like. Depending on the method used, it can be advantageous to carry out the cyclization in an inert organic solvent, for example, in an aromatic hydrocarbon such as toluene or the like, in an ether such as tetrahydrofuran or the like, in a halogenated hydrocarbon such as chloroform or the like, etc. The 4-(p-methoxybenzoylamino)butyric acid is a novel compound within the scope of the invention which can be prepared, for example, by acylating 4-aminobutyric acid. Acylation can be effected, for example, using p-methoxybenzoyl chloride as an acylating agent in the presence of an acid-binding agent such as sodium hydroxide.

According to process embodiment (e) above, 1-(p-methoxybenzoyl)-2-pyrrolidinone can be prepared by hydrolyzing a compound of formula III. The compounds of formula III can be conveniently prepared by reacting a compound of the formula

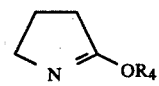

V wherein $R_4$ is as previously described, with p-methoxybenzoyl chloride. The resultant compound of formula III can be hydrolyzed in situ (i.e., without isolating it) to give the compound of formula I. The conversion of the compound of formula V to the compound of formula III and its subsequent hydrolysis to the compound of formula I are carried out using known methods. The reaction of the compound of formula V and p-methoxybenzoyl chloride is carried out in a suitable organic solvent such as benzene or the like, and, if necessary, in the presence of a strong base, for example, an alkali metal hydride such as lithium hydride.

Depending of the reaction conditions in the preparation of the N-acylated compound of formula III and its subsequent hydrolysis, there may be obtained, in addition to the desired 1-(p-methoxybenzoyl)-2-pyrrolidinone, varying amounts of the corresponding amidoalkyl ester which results from ring-opening. If the preparation of the compound of formula III is carried out in a water-immiscible solvent, then the subsequent hydrolysis produces predominantly the desired product.

As previously mentioned, the compound of formula III is not isolated, but rather is hydrolyzed in situ. The hydrolysis is carried out in a known manner by the addition of water, an aqueous alkali such as a lithium hydroxide solution or an aqueous acid such as an aqueous hydrochloric acid. The intermediates of formula III are also novel compounds within the scope of the invention.

As previously indicated, the 1-(p-methoxybenzoyl)-2-pyrrolidinone is a novel compound having valuable pharmacodynamic properties. The 1-(p-methoxybenzoyl)-2-pyrrolidinone has very low toxicity and has been shown to be capable of counteracting experimentally induced cerebral insufficiency in laboratory animals. The ability of the compound to counteract experimentally induced cerebral insufficiency was determined using the tests hereinafter described:

(A) POSTHYPERCAPNIC "AVOIDANCE" ACQUISITION

The test apparatus is a "shuttle box" having a 10 cm high hurdle in the middle and an electrifiable grid floor. A loudspeaker is mounted in the soundproof chamber. One group of 10 untrained rats (120–150 g.) is injected with a test preparation and a second group is injected with a control preparation. One or three hours after administration, each group is placed in a pure carbon dioxide environment for 12 seconds. A third group of 10 rats is treated neither with the test preparation nor with carbon dioxide. Three minutes after treatment with carbon dioxide the rats of all three groups must learn an escape response and an avoidance response in the "shuttle box" in the following sequence: 10 seconds silence—5 seconds noise ("avoidance response")—15 seconds noise+foot-shock ("escape response"). The sequence is repeated six times. For each of the six experiments the reaction time (time until the rat jumps over the hurdle) of each rat is measured and the statistical significance of the differences between the various mean group reaction times is calculated by means of the Mann-Whitney U-test.

An "active" dosage of a test preparation is a dosage which shows significant activity during the six experiments. Significant activity is exhibited when the mean reaction times of the animals treated with the test preparation and carbon dioxide are significantly better than those of the animals treated only with carbon dioxide and about equal to those of the animals treated neither with the test preparation nor with carbon dioxide.

(B) "PASSIVE AVOIDANCE" TEST WITH ELECTROSHOCK AMNESIA

The test apparatus is a Skinner box having an electrifiable grid floor with a grey quadrangular platform in one corner. Untrained male rats weighing 100–200 g are placed on the platform. When the rats climb down onto the grid floor they receive an electric shock. After 3–5 experiments, the rats exhibit a "passive avoidance response", that is, refusal to climb down from the platform. Immediately after acquisition of the passive avoidance response three groups of 20 rats each are formed. One group receives an electric shock (45 mA, 2 seconds) between the ears and an i.p. injection of sodium chloride. The second group receives an electric shock between the ears and an i.p. injection of the test preparation. The third group receives only an i.p. injection of sodium chloride. After three hours, each rat is placed on the platform once and the retention time, that is, the time the rat remains on the platform, (maximum 60 seconds), is measured. The significant activity of the test preparation in comparison to the two control groups is calculated by means of the Rang test.

An "active" dosage of a test preparation is a dosage which exhibits a significant protective activity against the electric shock. In other words, the animals treated with an active dosage of a test preparation and electric shock exhibit a relatively long retention time about equal to that of the animals not treated with electric shock, whereas the animals treated with sodium chloride and electric shock exhibit a relatively short retention time.

(C) INHIBITION OF THE HALOPERIDOL-INDUCED "KNOCK OUT" IN A "CONTINUOUS AVOIDANCE" TEST SEQUENCE

Male, untrained squirrel monkeys (Saimiri sciureus), each weighing 0.6 to 1.2 kg, are trained in a two-lever Skinner box in the following "continuous avoidance" sequence: "avoidance-shock"—interval 40 seconds; "shock-shock"—interval 20 seconds; foot-shock maximum 5 seconds. Monkeys having a normal baseline performance receive halo-peridol 1.0 mg/kg p.o. to determine the "knock-out" time (blocking of "avoidance" and "escape"). Monkeys having stable "knock-out" times are selected for the evaluation of test preparations as a potential cerebral insufficiency improver. The test preparations can be injected at various times before the treatment with haloperidol.

A dosage of a test preparation is considered to be active, if the administration before the treatment with haloperidol, produces a significant delay in the "knock-out" time. The test preparation is administered at different times prior to treatment with haloperidol.

(D) ANTI-ANOXIA TEST

Male rats weighing 300–350 g are tracheotomized under halothane anesthesia and an epidural cortical electrode is placed in each. After completion of the operation, the anesthesia is discontinued, all wounds and pressure points are infiltrated with xylocaine, d-tubocurarine is infused and the animal is artificially ventilated. The EEG is recorded continuously during the entire duration of the test. Anoxias are carried out at hourly intervals by ventilating the animal with 99.9% nitrogen until an isoelectric EEG is attained. After a period of 30 seconds with isoelectric EEG, the animal is again ventilated with normal room air.

The test parameters are defined as follows:
1. ST (survival time): Time to the attainment of an isoelectric EEG under nitrogen ventilation.
2. RT (recovery time): Time between further ventilation with room air and first electrical activity from the cortex.

The test preparations are administered 60 or 120 minutes before the first anoxia. The ST and RT values of treated rats are compared with placebo-treated controls by means of the Rang test. A lengthening of ST and/or shortening of RT is regarded as the protective activity against an anoxia.

An "active" dosage of a test preparation is a dosage which displays a significant protective activity.

In the previously described tests, the 1-(p-methoxybenzoyl)-2-pyrrolidinone, which has a very low acute toxicity [$LD_{50}$ > 5000 mg/kg p.o. (mice)], exhibits significant activity at the following dosages:

| Test | Minimum active dosage |
| --- | --- |
| A | 10 mg/kg i.p. (after 1 hr.) |
|   | 30 mg/kg p.o. (after 1 hr.) |
| B | 50 mg/kg i.p. |
| C | 1 mg/kg i.p. |
|   | 0.1 mg/kg p.o. |
| D | 20 mg/kg i.p. |

The 1-(p-methoxybenzoyl)-2-pyrrolidinone of formula I is useful in the control or prevention of cerebral insufficiency. Therefore, the 1-(p-methoxybenzoyl)-2-pyrrolidinone is useful as an agent for the treatment of cerebral insufficiency, for example, in cases of cerebral seizure, in geriatry (e.g. for improvement of geriatric cognitive processes) in alcoholism, etc. The dosage can vary within wide limits and is, or course, determined by individual requirements in each particular case. Generally, an orally administered daily dosage of about 10 mg. to 2500 mg. of 1-(p-methoxybenzoyl)-2-pyrrolidinone is suitable, although the upper limit can be exceeded if necessary, since the compound exhibits low toxicity.

Qualitatively, the 1-(p-methoxybenzoyl)-2-pyrrolidinone of formula I has a similar or better action than piracetam or HYDERGINE, which are known for their therapeutic use.

The 1-(p-methoxybenzoyl)-2-pyrrolidinone of formula I can be used as a medicament, for example in the form of pharmaceutical compositions. The pharmaceutical compositions can be administered orally, for example in the form of tablets, coated tablets, dragees, hard gelatin capsules, soft gelatin capsules, solutions, emulsions or suspensions. Alternatively, the compositions can be administered rectally, for example, in the form of suppositories, or parenterally, for example, in the form of injectable solutions.

In preparing the pharmaceutical compositions, the 1-(p-methoxybenzoyl)-2-pyrrolidinone is employed in association with pharmaceutically acceptable inert, inorganic or organic excipients. Suitable excipients for tablets, dragees and hard gelatin capsules include lactose, maize starch or derivatives thereof, talc, stearic acid or salts thereof etc. Suitable excipients for soft gelatin capsules include, for example, vegetable oils, waxes, fats, semi-solid and liquid polyols, etc. Suitable excipients for the preparation of solutions and syrups include, for example, water, polyols, saccharose, invert sugar, glucose and the like.

Suitable excipients for injection solutions include, for example, water, alcohols, polyols, glycerine, vegetable oils etc. Suitable excipients for suppositories include, for example, natural or hardened oils, waxes, fats, semi-solid or liquid polyols and the like.

The pharmaceutical compositions can also contain adjuvants such as preserving agents, solubilizing agents, stabilizing agents, wetting agents, emulsifying agents, sweetening agents, coloring agents, flavoring agents, salts for varying the osmotic pressure, buffers, coating agents or antioxidants, and other therapeutically valuable substances.

The following Examples further illustrate the invention. All temperatures are stated in degrees Centigrade, unless otherwise mentioned.

EXAMPLE 1

Preparation of 1-(p-methoxybenzoyl)-2-pyrrolidinone 40.0 g. of p-methoxybenzoyl chloride, 25.0 g. of 2-pyrrolidinone and 110 ml. of absolute diethyl ether are treated at between 0° C. and 10° C. while stirring with 52.5 ml. of triethylamine. The mixture is stirred at room temperature for a further 30 minutes and at reflux for 3 hours, then cooled down and treated at 2° C. with cold water. The insoluble constituents are filtered off under suction and washed with water and diethyl ether. The thus-obtained solid substance is recrystallized from alcohol after drying over phosphorus pentoxide. There is obtained 1-(p-methoxybenzoyl)-2-pyrrolidinone which melts at 121°–122° C.

EXAMPLE 2

Preparation of 1-(p-methoxybenzoyl)-2-pyrrolidinone 20.2 g. of the sodium salt of 2-pyrrolidinone (prepared using sodium hydride) suspended in 270 ml. of dimethylformamide are added in four portions at −10° C. to a solution of 37.0 g. of p-methoxybenzoyl chloride in 50 ml. of dimethylformamide. Subsequently, the mixture is stirred at room temperature for 1 hour and then at 40° C. for 4 hours. The solvent is evaporated and the residue is treated with diethyl ether and with cold sodium bicarbonate solution. The insoluble crystalline constituents are filtered off, washed with water and diethyl ether and dried in vacuo over phosphorus pentoxide. There is obtained 1-(p-methoxybenzoyl)-2-pyrrolidinone having a melting point of 120°–121° C.

EXAMPLE 3

Preparation of 1-(p-methoxybenzoyl)-2-pyrrolidinone 20 g. of p-methoxybenzoyl chloride and 20 g. of 2-pyrrolidinone are boiled at reflux in 20 ml. of diethyl ether for 16 hours and then diethyl ether, ice and 2-N aqueous ammonia are added to the mixture. The insoluble constituents are filtered off and washed ion-free with diethyl ether and water. The filter cake is dried and there is obtained 1-(p-methoxybenzoyl)-2-pyrrolidinone having a melting point of 119.5°–120.5° C.

EXAMPLE 4

Preparation of 1-(p-methoxybenzoyl)-2-pyrrolidinone

The procedure described in Example 3 is followed, but the starting materials are heated in 20 ml. of toluene instead of diethyl ether. The resulting 1-(p-methoxybenzoyl)-2-pyrrolidinone melts at 117°–118° C.

EXAMPLE 5

Preparation of 1-(p-methoxybenzoyl)-2-pyrrolidinone 10 g. of 2-pyrrolidinone and 10 g. of p-methoxybenzoyl chloride are heated at 80°–90° C. (internal temperature) in the absence of a solvent for 1 hour. The mixture is then left to cool down and is worked-up as described in Example 3. After recrystallization from alcohol, there is obtained 1-(p-methoxybenzoyl)-2-pyrrolidinone having a melting point of 120°–121° C.

EXAMPLE 6

Preparation of 1-(p-methoxybenzoyl)-2-pyrrolidinone 24.4 g. of p-methoxybenzoyl chloride and 22.5 g. of 1-trimethylsilyl-2-pyrrolidinone are mixed and the mixture is stirred at room temperature for 10 minutes. Then, the resulting trimethylchlorosilane is distilled off under reduced pressure in an oil bath at 80° C. The residue is triturated with 100 ml. of diethyl ether. The mixture is filtered and the filter cake is recrystallized from ethanol. There is obtained 1-(p-methoxybenzoyl)-2-pyrrolidinone having a melting point of 120°–121° C.

EXAMPLE 7

Preparation of 1-(p-methoxybenzoyl)-2-pyrrolidinone 7.0 g. of the sodium salt of 2-pyrrolidinone (prepared using sodium hydride) suspended in 120 ml. of dimethylformamide are added at −10° C. to a solution of 20.0 g. of p-methoxybenzoic acid pentachlorophenyl ester in 100 ml. of dimethylformamide. Subsequently, the mixture is stirred at room temperature for 1 hour and at 55° C. for 8 hours. The solvent is evaporated, the residue is treated with cold aqueous acetic acid solution and the mixture is extracted with ethyl acetate. The organic phase is washed with cold sodium bicarbonate solution and water, dried over sodium sulfate, filtered and evaporated. The residue is taken up in ethanol and stirred in an ice bath. The separated crystals are filtered off and there is obtained 1-(p-methoxybenzoyl)-2-pyrrolidinone having a melting point of 119°–120° C.

EXAMPLE 8

Preparation of 1-(p-benzyloxybenzoyl)-2-pyrrolidinone 15.9 g. of p-benzyloxybenzoyl chloride, 500 ml. of absolute diethyl ether and 6.3 ml. of 2-pyrrolidinone are treated with 13.4 ml. of triethylamine at 0° C. to 10° C. while stirring. The mixture is stirred at reflux for 9 hours, then cooled down and treated at 0° C. with cold water and ethyl acetate. The organic phase is washed with water, dried over sodium sulfate and evaporated. The residue is triturated with diethyl ether and the insoluble constituents are chromatographed over silica gel (particle size 0.2–0.5 mm). The constituents elutable with methylene chloride are triturated with diethyl ether. The insoluble constituents are filtered off and there is obtained 1-(p-benzyloxybenzoyl)-2-pyrrolidinone, having a melting point of 115°–117° C.

2.0 g. of 1-(p-benzyloxybenzoyl)-2-pyrrolidinone are hydrogenated in 20 ml. of absolute tetrahydrofuran and 20 ml. of absolute methanol over 300 mg. of palladium/carbon (5%) under atmospheric pressure and at room temperature. The catalyst is filtered off, the filtrate is concentrated and the residue is triturated with diethyl ether. After filtration, there is obtained 1-(p-hydroxybenzoyl)-2-pyrrolidinone, having a melting point of 179°–182° C.

150 mg. of 1-(p-hydroxybenzoyl)-2-pyrrolidinone are dissolved in 7 ml. of absolute tetrahydrofuran and then etheric diazomethane solution is added. The solvents are distilled off, the residue is triturated with diethyl ether and the mixture is filtered. There is obtained 1-(p-methoxybenzoyl)-2-pyrrolidinone which melts at 117.5°–119° C. after sublimation.

EXAMPLE 9

Preparation of 1-(p-methoxybenzoyl)-2-pyrrolidinone 10.0 g. of 5-oxo-3-pyrrolidinyl acetate and 8.82 ml. of trimethylchlorosilane are dissolved in 100 ml. of absolute tetrahydrofuran and then 9.65 ml. of triethylamine are added at −5° C. to 0° C. The temperature is held at −5° C. to 0° C. for 1 hour, the mixture is then filtered under an argon atmosphere, the filtrate is evaporated and the residue is distilled in vacuo. There is obtained 5-oxo-1-trimethylsilyl-3-pyrrolidinyl acetate, having a boiling point of 110° C./0.07 mmHg.

12.5 g. of 5-oxo-1-trimethylsilyl-3-pyrrolidinyl acetate are placed in 30 ml. of absolute tetrahydrofuran and then 9.90 g. of p-methoxybenzoyl chloride dissolved in 10 ml. of absolute tetrahydrofuran are added dropwise at 0°–10° C. The mixture is stirred at room temperature for 1 hour and at 70° C. for 1 hour and is then evaporated. The residue is dissolved in ethyl acetate and the ethyl acetate solution is washed with sodium chloride and sodium bicarbonate solution, dried over sodium sulfate and evaporated. 20 ml. of tetrahydrofuran and 20 ml. of saturated sodium bicarbonate solution are added to the residual viscous oil and the mixture obtained is then stirred at room temperature for 18 hours. The solvent mixture is decanted off and the residue is partitioned between water and methylene chloride. The organic phase is separated, dried over sodium sulfate and evaporated. The residual brown oil is chromatographed over silica gel (particle size 0.2–0.5 mm). The 1-(p-methoxybenzoyl)pyrrolin-2-one, which is eluted with benzene/diethyl ether (1:1) is recrystallized from alcohol and then has a melting point of 148°–150° C.

150 mg. of 1-(p-methoxybenzoyl)pyrrolin-2-one are dissolved in 100 ml. of ethyl acetate and hydrogenated over 30 mg. of 5% palladium/carbon with hydrogen at atmospheric pressure and room temperature. After filtering off the catalyst and evaporating the solvent, there is obtained 1-(p-methoxybenzoyl)-2-pyrrolidinone.

EXAMPLE 10

Preparation of 1-(p-methoxybenzoyl)-2-pyrrolidinone 10.2 g. of p-methoxybenzoyl chloride are added at 30° C. in one portion while stirring well to 30.9 g. of 4-amino-butyric acid, 24.0 g. of sodium hydroxide and 300 ml. of ion-free water. After 2 hours, the mixture is acidified with 75 ml. of concentrated hydrochloric acid at a temperature below 10° C. The precipitate is filtered off, washed ion-free with water, dried in a drying oven at 65° C. over phosphorus pentoxide and then recrystallized from 45 ml. of acetone/low-boiling petroleum ether (3:1). There is obtained 4-(p-methoxybenzoylamino)butyric acid having a melting point of 120.5°–122° C.

10 g. of phosphorus pentoxide and 6 ml. of orthophosphoric acid (at least 85%) are warmed with one another. 2.0 g. of 4-(p-methoxybenzoylamino)butyric acid are added at room temperature to the resulting solution. The mixture is warmed to 50° C. for 60 minutes, subsequently treated with ice and extracted with ethyl acetate. The organic phase is washed first with cold water, then with cold sodium bicarbonate solution and finally again with water and dried over sodium sulfate. The residue is triturated with diethyl ether and there is obtained 1-(p-methoxybenzoyl)-2-pyrrolidinone having a melting point of 120°–122° C.

EXAMPLE 11

Preparation of 1-(p-methoxybenzoyl)-2-pyrrolidinone 20.0 g. of 4-(p-methoxybenzoylamino)butyric acid, 50 ml. of toluene and 9.2 ml. of thionyl chloride are heated at reflux for 2 hours and then the mixture is treated with decolorizing charcoal and evaporated. The residue is dissolved in methylene chloride and chromatographed over neutral aluminum oxide. The 1-(p-methoxybenzoyl)-2-pyrrolidinone, which is eluted with methylene chloride, is recrystallized from alcohol and has a melting point of 119°–120° C.

EXAMPLE 12

Preparation of 1-(p-methoxybenzoyl)-2-pyrrolidinone 276 mg. of lithium hydride (98%), 40 ml. of benzene and 4.2 g. of 2-methoxypyrroline are boiled at reflux for 2 hours under nitrogen and while stirring well. After cooling to 25° C., 6.6 g. of p-methoxybenzoyl chloride dissolved in 25 ml. of benzene are added and the resulting mixture is stirred under reflux for 2 hours and at room temperature for 16 hours. 100 ml. of ethyl acetate followed by 3.0 g. of lithium hydroxide (98%) dissolved in 25 ml. of water are added to the mixture at room temperature within 15 minutes. The organic phase is washed neutral with water, dried over sodium sulfate and evaporated under reduced pressure. After recrystallization from ethanol, there is obtained 1-(p-methoxybenzoyl)-2-pyrrolidinone having a melting point of 119°–120° C.

EXAMPLE 13

Preparation of 1-(p-methoxybenzoyl)-2-pyrrolidinone 4.2 g. of 2-methoxypyrroline are dissolved in 25 ml. of benzene and treated at room temperature with 6.6 g. of p-methoxybenzoyl chloride dissolved in 30 ml. of benzene. The mixture is stirred at room temperature for 60 minutes and at reflux for 4 hours. 30 ml. of benzene are then added and the mixture is boiled at reflux for a further 24 hours. The volatile constituents are distilled off, the residue is taken up in ethanol, the mixture is concentrated, the residue is triturated with diethyl ether, filtered and the filter cake is taken up in ethyl acetate. The ethyl acetate solution is washed with sodium bicarbonate solution and water, dried over sodium sulfate and concentrated. The residue is sublimed in vacuo and there is obtained 1-(p-methoxybenzoyl)-2-pyrrolidinone having a melting point of 119°-120° C.

EXAMPLE 14

1-(p-methoxybenzoyl)-2-pyrrolidinone is used as the active substance for the manufacture of tablets of the following composition:

|  | Per Tablet |
| --- | --- |
| 1-(p-methoxybenzoyl)-2-pyrrolidinone (finely ground) | 100 mg. |
| Lactose (powdered) | 150 mg. |
| Maize starch (white) | 230 mg. |
| Polyvinylpyrrolidone | 15 mg. |
| Magnesium stearate | 5 mg. |
|  | 500 mg. |

The finely ground 1-(p-methoxybenzoyl)-2-pyrrolidinone, the powdered lactose and a part of the white maize starch are mixed with one another. The mixture is sieved, then moistened with a solution of polyvinylpyrrolidone in water, kneaded, moist granulated and dried. The granulate, the rest of the maize starch and the magnesium stearate are sieved and mixed with one another. The mixture is pressed to tablets of suitable form and size.

EXAMPLE 15

1-(p-methoxybenzoyl)-2-pyrrolidinone is used as the active substance for the manufacture of tablets of the following composition:

|  | Per Tablet |
| --- | --- |
| 1-(p-methoxybenzoyl)-2-pyrrolidinone (finely ground) | 100 mg. |
| Maize starch (white) | 160 mg. |
| Lactose | 50 mg. |
| Microcrystalline cellulose | 40 mg. |
| Polyvinylpyrrolidone | 20 mg. |
| Sodium carboxymethyl starch | 23 mg. |
| Magnesium stearate | 2 mg. |
|  | 395 mg. |

The finely ground 1-(p-methoxybenzoyl)-2-pyrrolidinone, a part of the white maize starch, the lactose, the microcrystalline cellulose and the polyvinylpyrrolidone are mixed with one another. The mixture is sieved and converted with the rest of the white maize starch and water into a granulate which is dried and sieved. The sodium carboxymethyl starch and the magnesium stearate are then added thereto, mixed and the mixture is pressed to tablets of suitable size, the tablets having a break-bar.

EXAMPLE 16

1-(p-methoxybenzoyl)-2-pyrrolidinone is used as the active substance for the manufacture of tablets of the following composition:

|  | Per Tablet |
| --- | --- |
| 1-(p-methoxybenzoyl)-2-pyrrolidinone (finely ground) | 500 mg. |
| Maize starch (white) | 270 mg. |
| Lactose | 80 mg. |
| Microcrystalline cellulose | 70 mg. |
| Polyvinylpyrrolidone | 35 mg. |
| Sodium carboxymethyl starch | 40 mg. |
| Magnesium stearate | 5 mg. |

|  | Per Tablet |
| --- | --- |
|  | 1000 mg. |

The finely ground 1-(p-methoxybenzoyl)-2-pyrrolidinone, a part of the white maize starch, the lactose, the microcrystalline cellulose and the polyvinylpyrrolidone are mixed with one another. The mixture is sieved and converted with the rest of the white maize starch and water into a granulate, which is dried and sieved. The sodium carboxymethyl starch and the magnesium stearate are then added thereto, mixed and the mixture is pressed to tablets of suitable size, the tablets having a break-bar.

EXAMPLE 17

1-(p-methoxybenzoyl)-2-pyrrolidinone is used as the active substance for the manufacture of duplex ampuls of the following composition:

| Active substance solution | | |
| --- | --- | --- |
| 1-(p-methoxybenzoyl)-2-pyrrolidinone |  | 100 mg. |
| Polyethyleneglycol | ad | 5 ml. |
| Diluent | | |
| Water for injection |  | 5 ml. |

Prior to the injection the diluent is added to the content of the 1-(p-methoxybenzoyl)-2-pyrrolidinone ampul. There are obtained 10 ml. of a ready-for-use injection solution containing 100 mg. of 1-(p-methoxybenzoyl)-2-pyrrolidinone.

EXAMPLE 18

1-(p-methoxybenzoyl)-2-pyrrolidinone is used as the active substance for the manufacture of duplex ampuls of the following composition:

| Active substance solution | | |
| --- | --- | --- |
| 1-(p-methoxybenzoyl)-2-pyrrolidinone |  | 100 mg. |
| Glycofurol | ad | 3.5 ml. |
| Diluent | | |
| Sodium chloride |  | 67.5 mg. |
| Water for injection | ad | 6.5 ml. |

Prior to the injection the diluent is added to the content of the 1-(p-methoxybenzoyl)-2-pyrrolidinone ampul. There are obtained 10 ml. of a ready-for-use injection solution containing 100 mg. of 1-(p-methoxybenzoyl)-2-pyrrolidinone.

EXAMPLE 19

1-(p-methoxybenzoyl)-2-pyrrolidinone is used as the active substance for the manufacture of duplex ampuls of the following composition:

| Active substance solution | | |
| --- | --- | --- |
| 1-(p-methoxybenzoyl)-2-pyrrolidinone |  | 100 mg. |
| Polyethyleneglycol |  | 1.5 ml. |
| Glycofurol | ad | 4 ml. |
| Diluent | | |
| Water for injection |  | 6 ml. |

Prior to the injection the diluent is added to the content of the 1-(p-methoxybenzoyl)-2-pyrrolidinone ampul. There are obtained 10 ml. of a ready-for-use injection solution containing 100 mg. of 1-(p-methoxybenzoyl)-2-pyrrolidinone.

We claim:
1. 1-(p-Methoxybenzoyl)-2-pyrrolidinone.
2. 1-(p-Hydroxybenzoyl)-2-pyrrolidinone.
3. 1-(p-Benzyloxybenzoyl)-2-pyrrolidinone.

* * * * *